United States Patent
Spence et al.

(10) Patent No.: US 9,381,286 B2
(45) Date of Patent: Jul. 5, 2016

(54) GRAFT FOR USE WITH COUNTERPULSATION DEVICE

(71) Applicant: Abiomed, Inc., Danvers, MA (US)

(72) Inventors: Paul Spence, Louisville, KY (US); Rob Dowling, Louisville, KY (US); Robert T. V. Kung, Andover, MA (US); Caitlyn Hastie, Billerica, MA (US); Thorsten Siess, Wuerselen (DE); Eric Gratz, Louisville, KY (US); Gerd Spanier, Aachen (DE)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 14/360,470

(22) PCT Filed: Nov. 21, 2012

(86) PCT No.: PCT/US2012/066292
§ 371 (c)(1),
(2) Date: May 23, 2014

(87) PCT Pub. No.: WO2013/078338
PCT Pub. Date: May 30, 2013

(65) Prior Publication Data
US 2014/0316189 A1    Oct. 23, 2014

Related U.S. Application Data

(60) Provisional application No. 61/563,238, filed on Nov. 23, 2011.

(51) Int. Cl.
*A61M 1/10* (2006.01)
*A61M 1/12* (2006.01)
(Continued)

(52) U.S. Cl.
CPC .............. *A61M 1/1086* (2013.01); *A61M 1/10* (2013.01); *A61M 1/106* (2013.01); *A61M 1/107* (2013.01);
(Continued)

(58) Field of Classification Search
CPC ... A61M 1/122; A61M 1/107; A61M 1/1037; A61M 1/12; A61M 1/1072; A61M 1/125; A61M 1/1086; A61M 2205/33; A61M 1/1005; A61M 1/1053; A61M 1/10; A61M 37/00; A61M 2039/0279; A61M 25/0043; A61M 39/0247; A61B 5/14865; A61B 2560/04; A61F 2/06; A61F 2002/068; A61F 2/064; F04B 43/06; A61N 1/059; A61N 1/326
See application file for complete search history.

(56) References Cited

U.S. PATENT DOCUMENTS 4,240,409 A    12/1980   Robinson et al.
4,573,576 A    3/1986    Krol
(Continued)

FOREIGN PATENT DOCUMENTS

WO    WO-2013023009    2/2013

OTHER PUBLICATIONS

PCT International Search Report for International Application No. PCT/US12/66292, mailed Feb. 5, 2013 (3 pages).
(Continued)

*Primary Examiner* — Deborah Malamud
(74) *Attorney, Agent, or Firm* — Ropes & Gray LLP

(57) ABSTRACT

An apparatus is disclosed for attaching a counter pulsation device (CPD) to a blood vessel in a human or animal subject, the apparatus including: an interposition graft having a first end configured to be attached to the blood vessel, a second end, and an interior passage providing fluid connection between the first end and the second end; and a pump graft having first end attached to the second end of the interposition graft, a second end configured to be attached to the CPD, and an interior passage providing fluid connection between the first end and the second end In some embodiments, the interior passage of the interposition graft includes a rough surface configured to promote biological growth on the surface, and the interior passage of the pump graft includes a smooth surface configured to inhibit biological growth on the surface.

32 Claims, 13 Drawing Sheets

(51) Int. Cl.
*A61B 17/062* (2006.01)
*A61B 17/11* (2006.01)

(52) U.S. Cl.
CPC ........... *A61M 1/1008* (2014.02); *A61M 1/1044* (2014.02); *A61M 1/122* (2014.02); *A61B 17/062* (2013.01); *A61B 2017/1107* (2013.01); *A61B 2017/1135* (2013.01)

(56) References Cited

U.S. PATENT DOCUMENTS

| | | |
|---|---|---|
| 5,084,064 A | 1/1992 | Barak et al. |
| 5,327,885 A | 7/1994 | Griffith |
| 6,050,975 A | 4/2000 | Poirier |
| 6,390,969 B1 | 5/2002 | Bolling et al. |
| 6,524,322 B1 | 2/2003 | Berreklouw |
| 2002/0095210 A1 | 7/2002 | Finnegan et al. |
| 2005/0119573 A1 | 6/2005 | Vilenkin |
| 2006/0020242 A1 | 1/2006 | Yamazaki |
| 2007/0208290 A1 | 9/2007 | Pecor |
| 2009/0048663 A1 | 2/2009 | Greenberg |
| 2010/0280306 A1 | 11/2010 | Spence |
| 2010/0324667 A1 | 12/2010 | King |
| 2015/0265757 A1 | 9/2015 | Dowling |

OTHER PUBLICATIONS

PCT International Search Report for International Application No. PCT/US12/50604, mailed Oct. 23, 2012 (3 pages).

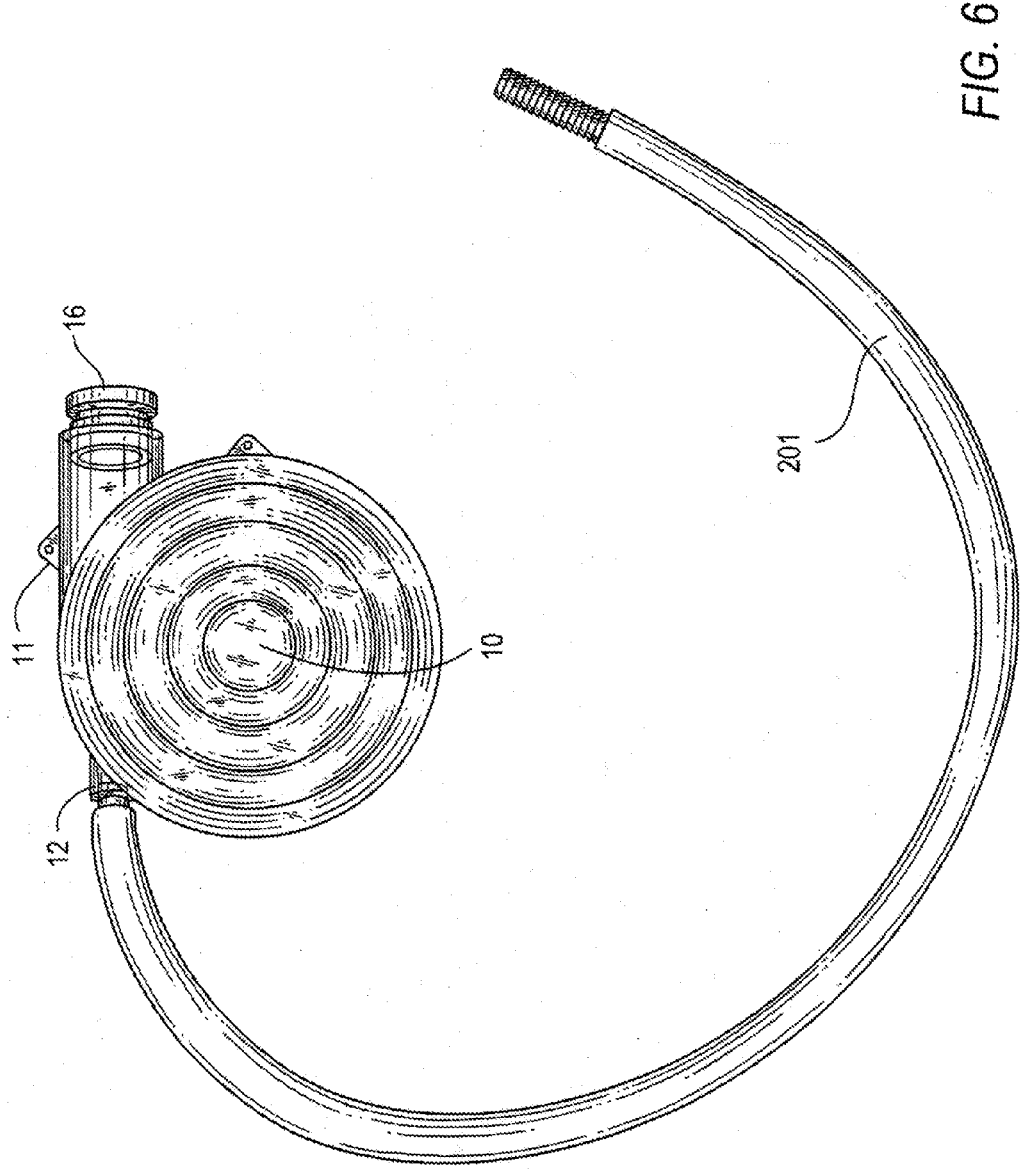

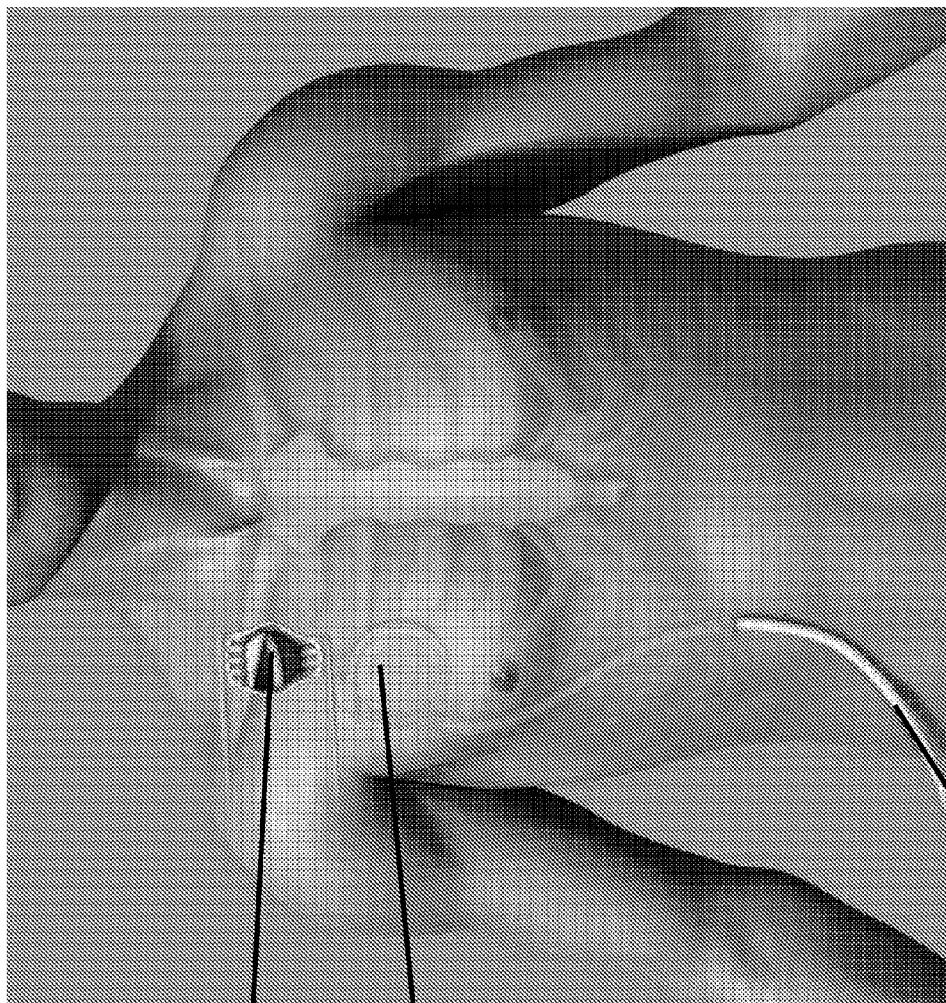

GRAFT FOR USE WITH COUNTERPULSATION DEVICE

RELATED APPLICATIONS

This application is the U.S. National Stage of International Application Number PCT/US2012/066292, filed Nov. 21, 2012, which claims priority to U.S. Provisional Patent Application No. 61/563,238, filed Nov. 23, 2011. The entire contents of the foregoing applications are hereby incorporated herein by reference.

BACKGROUND

The following section is presented for informational purposes only. The inclusion of material in this section should not be considered to be an admission that such material is prior art to the present application.

Cardiac disorders such as congestive heart failure affect more than five million patients in the United States alone. Many patients suffering from such disorders require mechanical circulatory support. Counterpulsation therapy maybe used for the treatment of cardiac disorders. Counterpulsation is a technique that synchronizes the external pumping of blood with the heart's cycle to assist the circulation and decreasing the work of the heart. Counterpulsation pumps eject when the heart is filling (relaxation period) to increase blood flow and oxygen to the heart. Counterpulsation pumps fill when the heart is ejecting to decrease the hearts workload and lessen oxygen demand.

Counterpulsation may be implemented using an implanted pump device, referred to as a counterpulsation device (CPD). The pumping action of the CPD may be synched to the patient's heartbeat to provide counterpulsation, e.g. using a detected EKG signal.

SUMMARY

The applicants have developed devices, systems, and methods as described herein for use with counterpulsation devices (CPDs).

In one aspect, an apparatus is disclosed for attaching a counter pulsation device (CPD) to a blood vessel in a human or animal subject, the apparatus including: an interposition graft having a first end configured to be attached to the blood vessel, a second end, and an interior passage providing fluid connection between the first end and the second end; and a pump graft having first end attached to the second end of the interposition graft, a second end configured to be attached to the CPD, and an interior passage providing fluid connection between the first end and the second end In some embodiments, the interior passage of the interposition graft includes a rough surface configured to promote biological growth on the rough surface, and the interior passage of the pump graft includes a smooth surface configured to inhibit biological growth on the smooth surface.

In some embodiments, the interposition graft is shaped to prevent contact between the rough surface and the smooth surface to inhibit biological growth from the rough surface onto the smooth surface.

In some embodiments, the interior passage of the interposition graft has a region of increased diameter located proximal to the second end of the interposition graft configured such that the first end of the pump graft extends into the interior passage of the interposition graft without making physical contact with the rough surface.

In some embodiments, the second end of the interposition graft includes a first sewing ring, and the first end of the pump graft includes a second sewing ring. In some embodiments, the first and second sewing rings are attached to each other.

In some embodiments, the interposition graft and/or the pump graft are substantially flexible.

In some embodiments, the rough surface includes a fabric material. In some embodiments, the fabric material includes a fabric including polymer fibers. In some embodiments, the fibers include polyester fibers.

In some embodiments, the pump graft includes an expanded or molded material, e.g., a thermoplastic polymer. In some embodiments, the polymer includes a fluoropolymer (e.g., polytetrafluoroethylene).

In another aspect, a method is disclosed for attaching a counter pulsation device (CPD) to a blood vessel in a human or animal subject, the method including: obtaining an interposition graft having a first end configured to be attached to the blood vessel, a second end, and an interior passage providing fluid connection between the first end and the second end; and obtaining a pump graft having first end attached to the second end of the interposition graft, a second end configured to be attached to the CPD, and an interior passage providing fluid connection between the first end and the second end. In some embodiments, the interior passage of the interposition graft includes a rough surface configured to promote biological growth on the rough surface; and the interior passage of the pump graft includes a smooth surface configured to inhibit biological growth on the smooth surface. Some embodiments include attaching the first end of the interposition graft to the blood vessel; attaching the second end of the interposition graft to the first end of the pump graft; and attaching the second end of the pump graft to the CPD.

In some embodiments, the interposition graft is shaped to prevent contact between the rough surface and the smooth surface to inhibit biological growth from the rough surface onto the smooth surface.

In some embodiments, the interior passage of the interposition graft has a region of increased diameter located proximal to the second end of the interposition graft. Some embodiments include attaching the second end of the interposition graft to the first end of the pump graft such that the first end pump graft extends into the interior passage of the interposition graft without making physical contact with the rough surface.

In some embodiments, the second end of the interposition graft includes a first sewing ring, and the first end of the pump graft includes a second sewing ring, and attaching the second end of the interposition graft to the first end of the pump graft includes sewing the first and second sewing rings to each other.

In some embodiments, the interposition graft and/or the pump graft are substantially flexible. Some embodiments include, during the step of attaching the first end of the interposition graft to the blood vessel, flexing the interposition graft. In some embodiments, flexing the interposition graft includes flexing the graft to provide increased visibility of the blood vessel.

In some embodiments, the rough surface includes a fabric material. In some embodiments, the fabric material includes a fabric including polymer fibers. In some embodiments, the fibers include polyester fibers.

In some embodiments, the pump graft includes an expanded or molded material, e.g., a thermoplastic polymer. In some embodiments, the polymer includes a fluoropolymer (e.g., polytetrafluoroethylene).

In some embodiments, the blood vessel includes the subclavian artery.

Some embodiments include implanting the CPD in the subject. In some embodiments, the CPD is implanted superficially outside of a chest cavity of the subject, and the pump and interposition graft provides fluid communication between the CPD and the blood vessel within the chest cavity.

In another aspect, a kit is disclosed for attaching a counter pulsation device (CPD) to a blood vessel including: an interposition graft having a first end configured to be attached to the blood vessel, a second end, and an interior passage providing fluid connection between the first end and the second end; and a pump graft having first end configured to be attached to the second end of the interposition graft, a second end configured to be attached to the CPD, and an interior passage providing fluid connection between the first end and the second end. In some embodiments, the interior passage of the interposition graft includes a rough surface configured to promote biological growth on the rough surface; and the interior passage of the pump graft includes a smooth surface configured to inhibit biological growth on the smooth surface.

In some embodiments, the interposition graft is shaped to prevent contact between the rough surface and the smooth surface to inhibit biological growth from the rough surface onto the smooth surface.

In some embodiments, the interior passage of the interposition graft has a region of increased diameter located proximal to the second of the interposition graft configured such that the first end of the pump graft extends into the interior passage of the interposition graft without making physical contact with the rough surface.

In some embodiments, the second end of the interposition graft includes a first sewing ring, and the first end of the pump graft includes a second sewing ring. In some embodiments, the first and second sewing rings are configured to be attached to each other.

In some embodiments, the rough surface includes a fabric material. In some embodiments, the fabric material includes a fabric including polymer fibers. In some embodiments, the fibers include polyester fibers.

In some embodiments, the pump graft includes an expanded or molded material, e.g., a thermoplastic polymer. In some embodiments, the polymer includes a fluoropolymer (e.g., polytetrafluoroethylene).

In another aspect, a system is disclosed including: a counterpulsation device (CPD); an apparatus of any one the types described above, where the apparatus is configured for attaching the CPD to a blood vessel in a human or animal subject. Some embodiment including a drive line providing pneumatic communication between the CPD and a CPD driver. Some embodiments include the CPD driver.

Various embodiments may include any of the elements described above, alone or in any suitable combination.

BRIEF DESCRIPTION OF DRAWINGS

The accompanying drawings are presented for illustrative purposes only and are not intended to be drawn to scale.

FIG. 6 is a photograph of a CPD with an attached drive line.

FIGS. 7A-7F illustrate the implantation of a CPD device in a human subject.

DETAILED DESCRIPTION

The following disclosure describes a graft and related methods for use with an implantable counterpulsation device (CPD).

Figure 1:
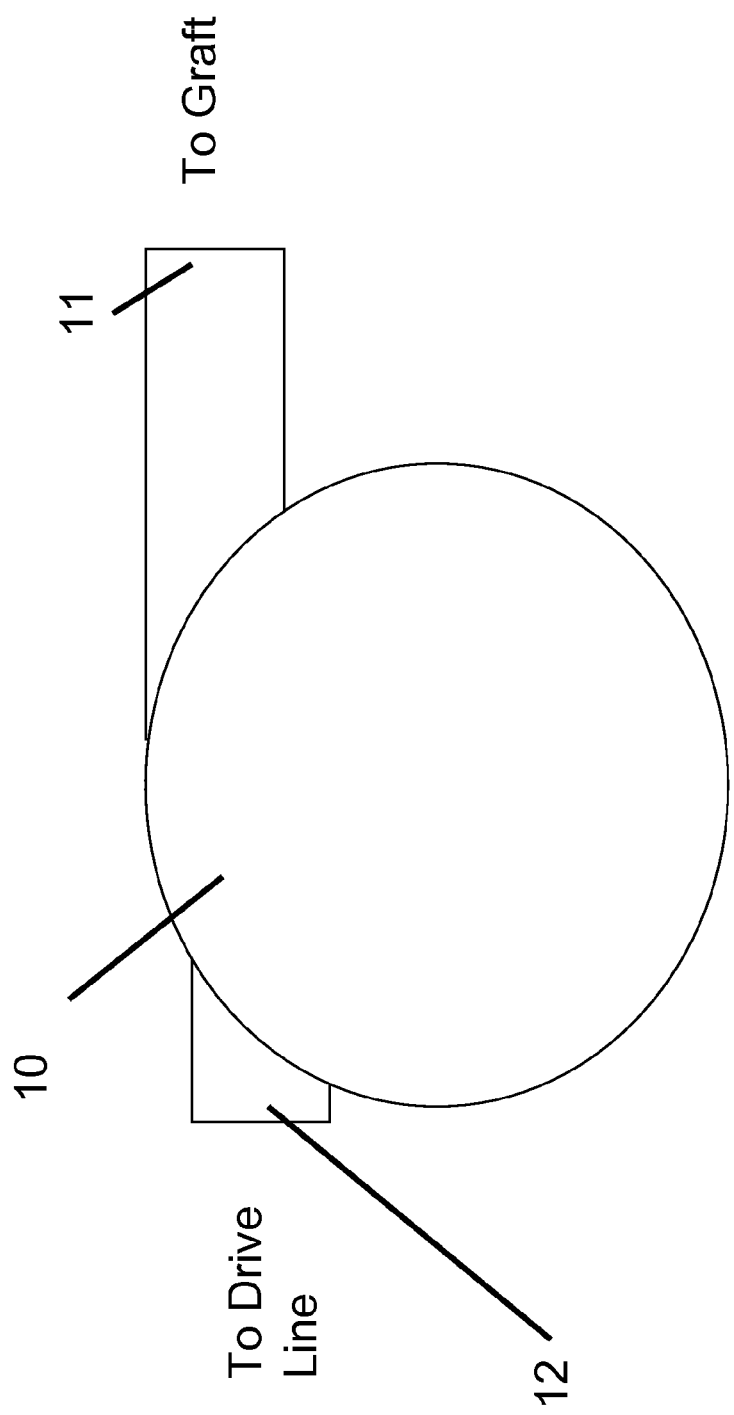
FIG. 1 is an illustration of a counterpulsation device (CPD).

FIG. 1 shows an exemplary embodiment of a CPD 10. The CPD 10 has a pump port 11 that can be attached to blood vessel of a subject using a graft 100 (not shown, described below). The pump port 11 allows for inflow and outflow of blood from the CPD 10. The CPD 10 also includes a drive line port 12, that can receive a drive line 201 (not shown, described below) that may control the operation of the CPD 10, e.g., as detailed below. In some embodiments, the CPD 10 may include a blood pump, e.g., a valveless pump, in fluid communication with the pump port 11. In some embodiments, the CPD includes a blood chamber that is separated from a drive chamber by a membrane. The drive chamber is in pneumatic communication with the driveline, while the blood chamber is in fluid communication with the blood vessel via the graft 100.

In some embodiments, the CPD 10 may be of the type available under the Symphony® product line available from Abiomed, Inc. of Danvers, Mass.

Figure 2:
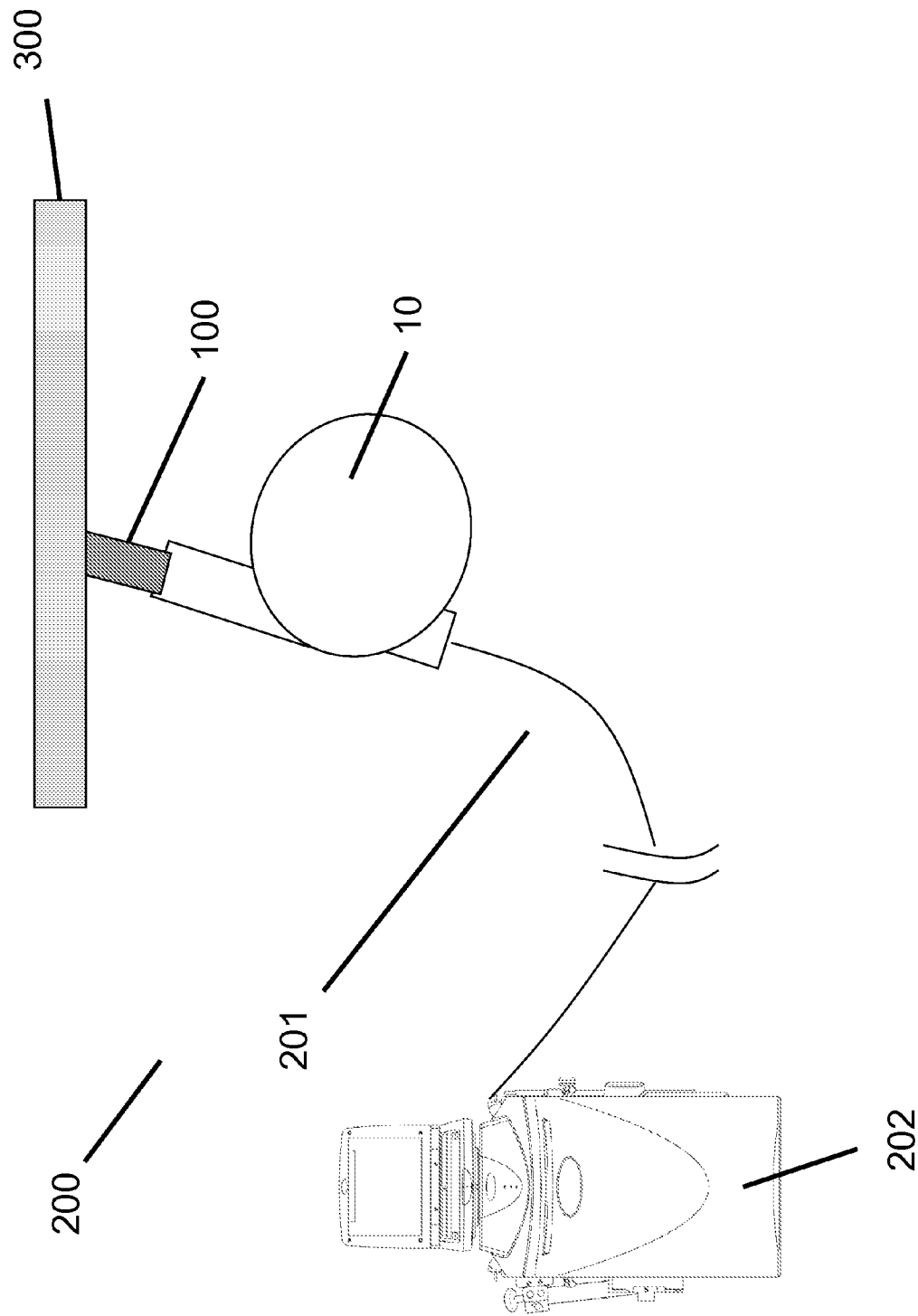
FIG. 2 is an illustration of a CPD system including a CPD, CPD driver, and CPD graft.

FIG. 2 shows an exemplary CPD system 200 used to provide counterpulsation therapy to a subject. The CPD 10 is attached to a blood vessel 300 (e.g., the subclavian artery) using a graft 100, e.g., of the type described below. As detailed below, in some embodiments, the CPD may be implanted in the subject, e.g., superficially in a so called "pacemaker pocket" outside of the chest cavity of the subject, with the graft 100 providing fluid communication between the CPD and the blood vessel 300 within the chest cavity.

A drive line 201 (e.g., a pneumatic line) attaches the CPD 10 to a drive controller 202, to allow for control of the operation of the CPD 10. For example, in some embodiments, the drive controller 202 synchronizes the external pumping of blood from the CPD 10 with the subject's heart's cycle to assist the circulation and decrease the work of the heart. The controller may cause the CPD 10 to eject blood when the heart is relaxing to increase blood flow and oxygen to the heart, and to fill the pump passively or actively when the heart is contracting to eject blood to decrease the heart's workload and lessen oxygen demand. For example the drive controller 202 may alternately apply positive pressure and vacuum through the drive line 201 to empty and fill the CPD 10. The pumping action of the CPD 10 may be synched to the patient's heartbeat to provide counterpulsation, e.g. using a detected EKG signal sent to the drive controller 202.

Figure 3:
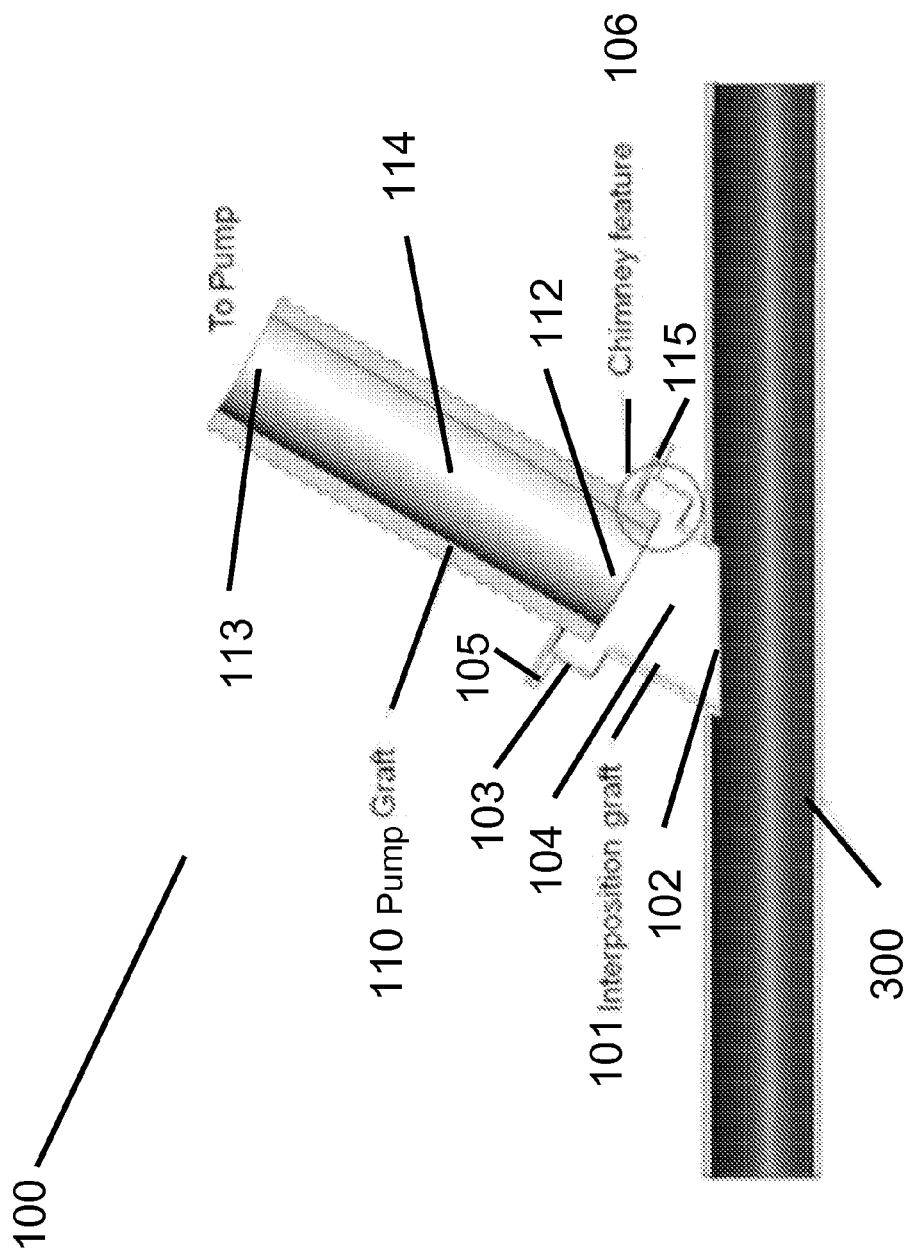
FIG. 3 is an illustration of a CPD graft.

FIG. 3 shows a detailed view of an embodiment the graft 100. The graft 100 is made up of a interposition graft 101 and a pump graft 110. The interposition graft 101 has a first end 102 attached using any suitable anastomosis technique to the blood vessel 300 and a second end 103 attached to the pump graft 110. For example, in some embodiments, the interposition graft 101 is sewn to the vessel 300. An interior passage 104 (e.g. a tubular passage) is formed in the interposition graft 101 that provides fluid communication with the pump graft 110.

In some embodiments, the graft 100 may include one or more of the connectors described in U.S. Pat. Pub. No. 2012/0209057 published Aug. 16, 2012 and entitled Lockable Quick Coupling, the entire contents of which are incorporated herein by reference.

The pump graft 110 has a first end 112 that attaches to the second end 103 of the interposition graft 101 using any suitable attachment technique. As shown, the interposition graft 101 and pump graft 110 each include a sewing ring 105 and 115 (respectively). These rings can be sewn together to attach the interposition and pump grafts 101 and 110.

The pump graft 110 has a second end 113 that attaches to the CPD 10 (not shown) using any suitable connector (not shown). For example, FIG. 5, described in greater detail below, shows an embodiment of the pump graft 110 featuring a metal (as shown titanium) screw on type connector.

An interior passage 114 (e.g. a tubular passage) is formed in the pump graft 110 that provides fluid communication with the CPD 10. Accordingly, when fully assembled, the graft 100 provides fluid communication from the vessel 300 through the interposition graft 101 and the pump graft 110 to the CPD 10.

In some embodiments, the graft 100 is configured to promote biological tissue growth on and around the interposition graft 101 (e.g., to improve connection to the vessel 100), while inhibiting tissue growth onto the pump graft 110 (e.g., to avoid interference with the operation of the CPD).

In some embodiments, this arrangement is advantageous for use with the CPD 10, e.g., in cases where blood flow both enters and exits the CPD 10 through the connection via graft 100 with vessel 300. Embodiments of the graft 100 described herein may advantageously provide hemocompatibility for flow in both directions, by promoting good washing through the graft and preventing or reducing thrombus formation.

This arrangement is in contrast to other blood pump devices such as ventricular assist devices (VADs). Typically, VADs have separate inflow and outflow conduits, and so do not require a graft connection of the type described herein.

In some embodiments, the interior passage 104 (and/or other surfaces) of the interposition graft 101 includes a rough surface configured to promote biological growth on the surface. In some embodiments, the rough surface includes a fabric material. In some embodiments, the fabric material includes a fabric including polymer fibers. In some embodiments, the fibers include polyester fibers. For example, in some embodiments, the interposition graft 101 may be constructed from a length of DACRON® fabric familiar to those skilled in the art.

In some embodiments, the interior passage 114 of the pump graft 110 includes a smooth or substantially smooth surface configured to inhibit biological growth on the surface. For example in some embodiments, the pump graft 110 may be made of a plastic or other suitable material, e.g., a molded and/or expanded thermoplastic polymer. In some embodiments, the polymer includes a fluoropolymer, e.g., polytetrafluoroethylene (PTFE). In some embodiments, the interior passage 114 of the pump graft 110 may be coated (e.g., using a silicone coating) to further enhance the smoothness of the passage.

In some embodiments, the physical shape of the interposition graft 101 and/or the pump graft 110 may be designed to prevent tissue ingrowth into the interior passage 114 of the pump graft 110. For example, as shown the interposition graft 101 is shaped to prevent contact between the rough surface or surfaces of the interposition graft 101 and the smooth surface of the interior passage 114 of the pump graft 110. The interior passage 104 of the interposition graft 101 has a so called "chimney feature" 106, a region of increased diameter located proximal to the connection with the pump graft 110. The chimney feature 106 is positioned such that the first end 112 of the pump graft 110 extends into the interior passage 104 of the interposition graft 101 without making physical contact with any rough surface. In some embodiments this may inhibit or substantially prevent tissue ingrowth into the inner passage 114 of the pump graft 110.

In typical cases, the surgical access to the vessel 110 (e.g., the subclavian artery) may be limited and the visibility is restricted. To compensate for this, in some embodiments, the interposition graft 101 is made of a flexible material to allow it to be deformed. This allows the surgeon to see the cut edges of the artery while performing anastomosis of the interposition graft 101. After the anastomosis of the interposition graft 110 is complete, the pump graft 110 is attached to the interposition graft, e.g. using the sewing 105 and 115 or any other suitable technique. In some embodiments the elasticity of the interposition graft 101 sufficient to keep the interface between vessel and graft open i.e. during the filling period of the pump In some embodiments, the length of the interposition graft 101 along the dimension from end 102 to end 103 may be shorter than the length of the pump graft 110 along the dimension from end 112 to end 113. For example, in some embodiments the length of the pump graft 110 may be at least 1.25, 1.5, 1.75, 2.0, 2.5, 3.0, 3.5, 4.0, 4.5, 5.0, 5.5, 6.0 or more times the length of the interposition graft.

Figure 4A:
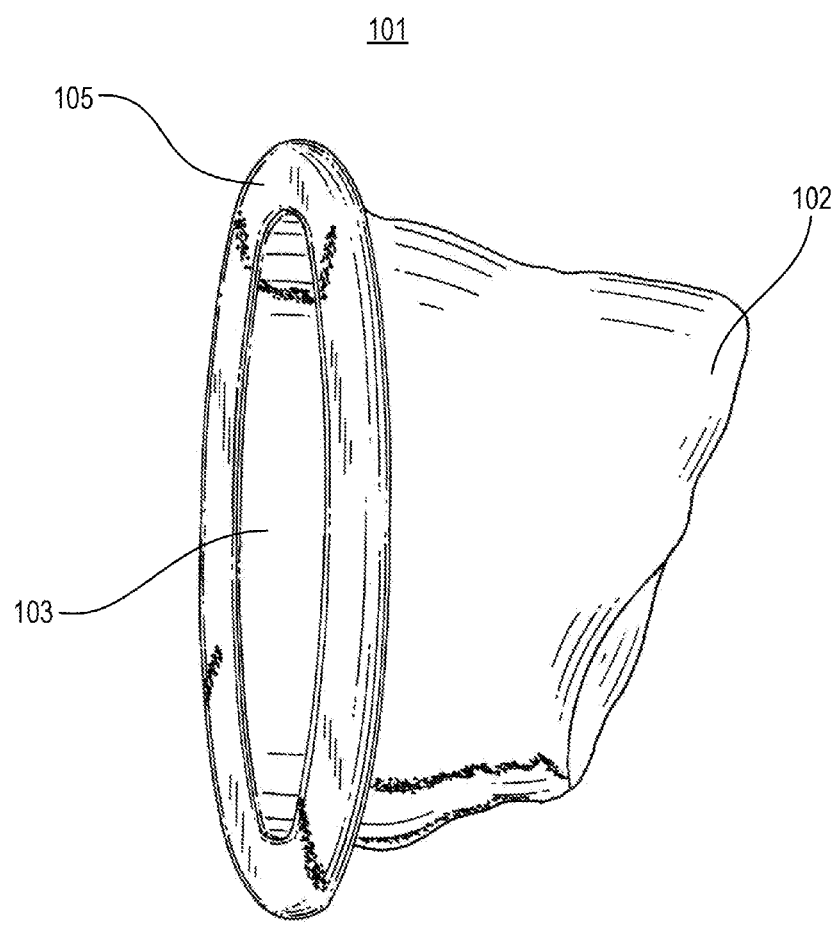
FIGS. 4A and 4B are photographs of an interposition graft for a CPD graft.
Figure 4B:
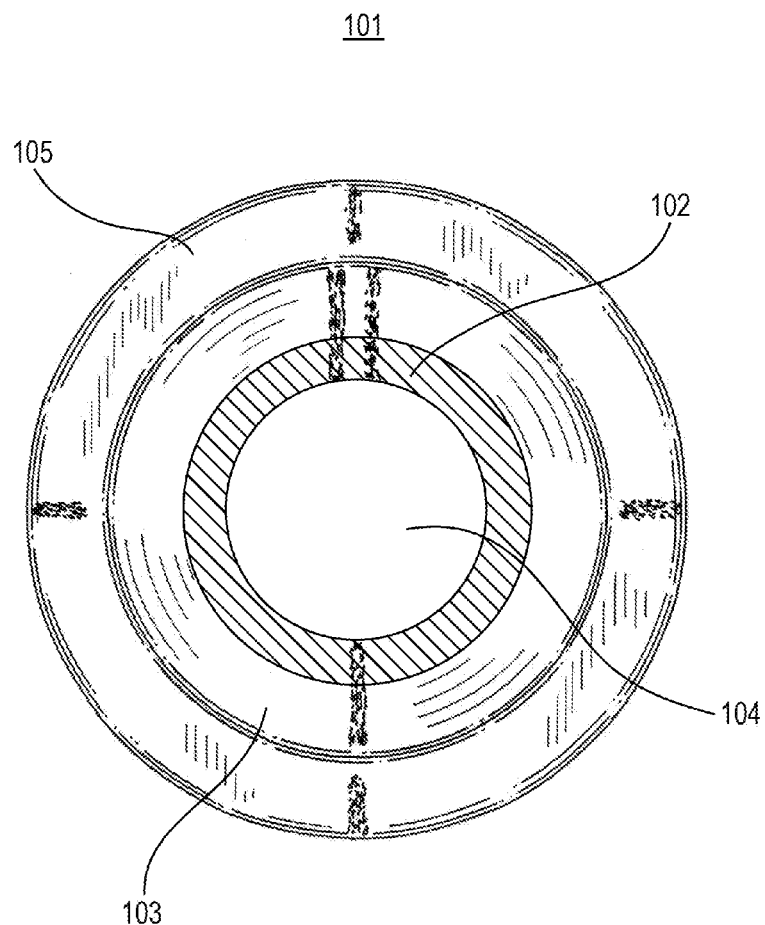

FIGS. 4A and 4B show photographic views (side and head on, respectively) of an exemplary embodiment of the interposition graft 101. As shown, the interposition graft 101 in constructed from DACRON® fabric. The fabric includes a partial silicone coating of the outer surface of the interposition graft 101. As described above the inner surface along the passage 104 is uncoated and rough to promote tissue ingrowth. The end 102 is beveled to aid in proper alignment when attached to the vessel 300.

Figure 5:
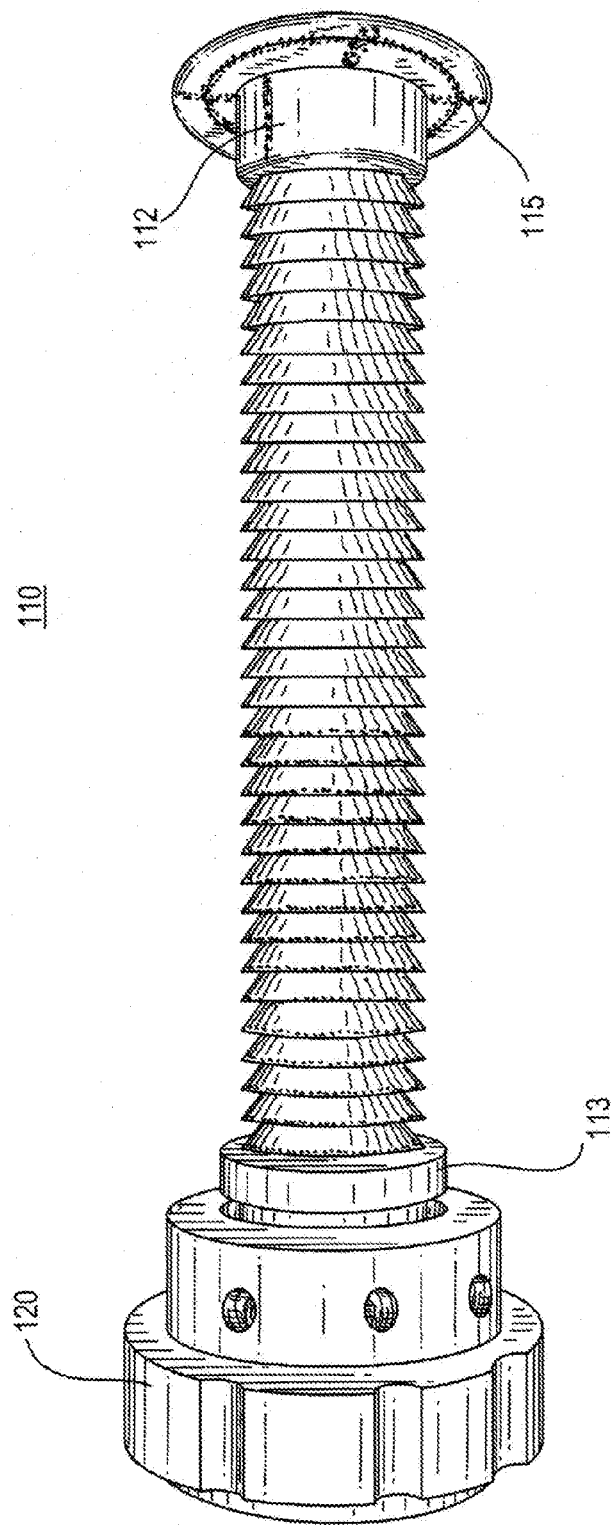
FIG. 5 is a photograph of a pump graft for a CPD graft.

FIG. 5 shows a photographic view of an exemplary embodiment of the pump graft 110. The pump graft 110 is constructed from an expanded PTFE material. Although the exterior of the graft 110 has a grooved or accordion shape, the inner passage 114 (not shown) is smooth and free or substantially free of features that may encourage tissue growth. The inner passage 114 of the pump graft 110 may be (as shown) coated with silicone to improve smoothness. The pump graft 110 includes a metal (as shown titanium) screw on type connector 120 for attachment to the CPD 10. A sewing ring 115 is provided for attachment to the interposition graft 101.

The pump graft 110 may be of any suitable length, e.g., in the range of about 3 cm to about 10 cm or any subrange thereof. In some embodiments, a various length grafts may be provided so that a length best suited to the subject's physiology may be selected. For example in some embodiments, grafts with length of 4.5 cm, 5.5 cm, and 7 cm may be provided.

As shown in FIGS. 4A, 4B, and 5, the grafts 101 and 110 may be pre-marked with indicia to aid in proper alignment. The grafts may also include indicia to guide suturing, to help ensure that the end 112 of the pump graft is properly centered within the inner passage 104 of the interposition graft 101. As noted above, this may promote good washing through the graft and prevent or reduce thrombus formation.

FIG. 6 shows a photographic view of an exemplary embodiment of the CPD 10 with drive line 201 attached to drive line port 12. The pump port 11 includes a titanium connector 13 used to attach to connector 16 shown in FIG. 5. In the embodiment shown in FIG. 6, the CPD 10 includes a valveless pump capable of pumping at a rate of about 3.0 liters per minute or more, at a pulse rate of about 100 beats per minute or more.

In some embodiments, some or all of the above described components (e.g., the interposer graft 110 and pump graft 110) may be provided unassembled in a kit. In some embodiments the kit may include instruction for assembly and use, e.g., stored in a printed or electronic media.

FIGS. 7A-7F illustrate an exemplary method implantation of the CPD 10 in a human subject using the graft 100.

Figure 7A:
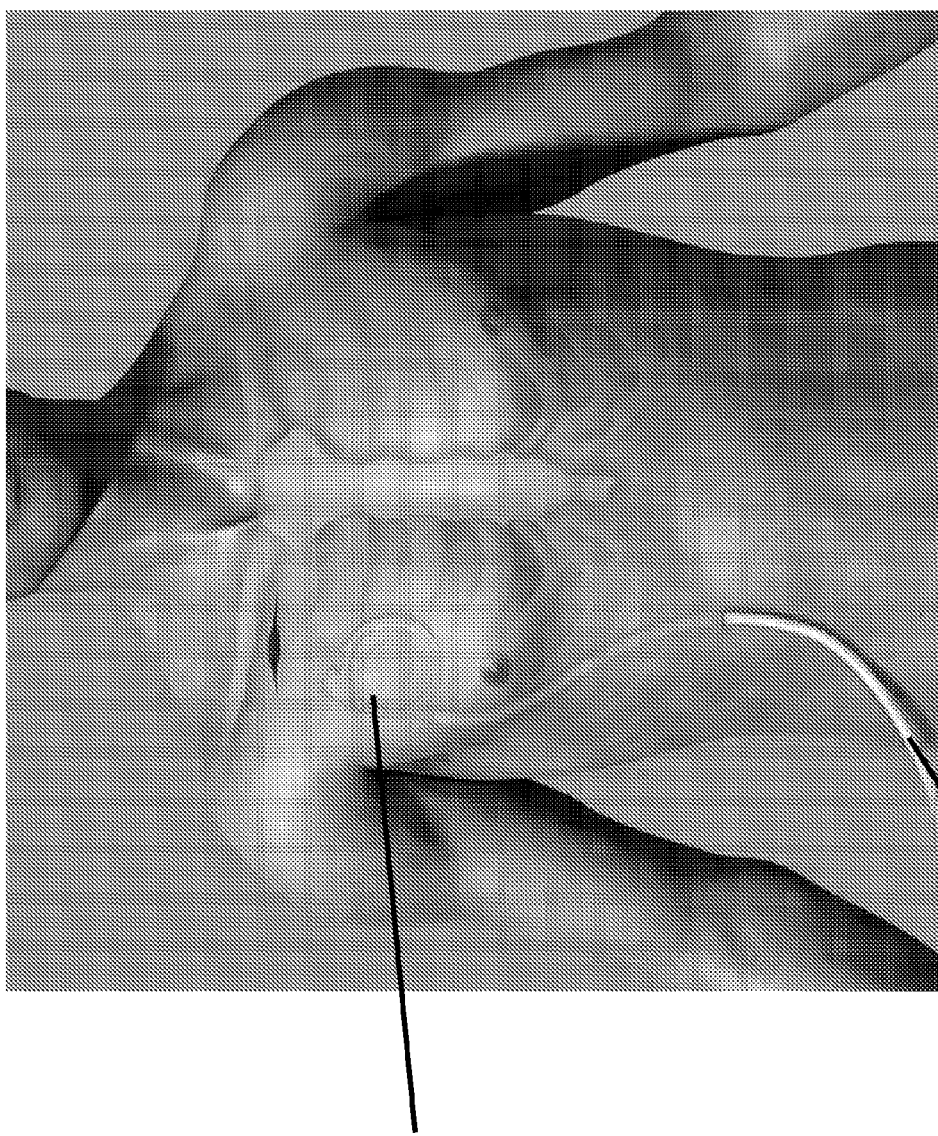

Referring to FIG. 7A, a pump pocket is made in the subcutaneous tissue above or below the pectoralis fascia, in a plane similar to or parallel to that used for pacemaker placement. In some embodiments, a fit model of the CPD 10 may be used to properly size the pocket. The CPD 10 is placed in the pocket, with the drive line 201 externalized (e.g., using a biopsy punch tool, tunneling tool, or other suitable implement).

Referring to FIG. 7B, the subclavian artery 300 is exposed, e.g., using techniques known in the art. Proximal and distal clamps are placed on the subclavian artery 300, and an arteriotomy is performed.

Figure 7C:
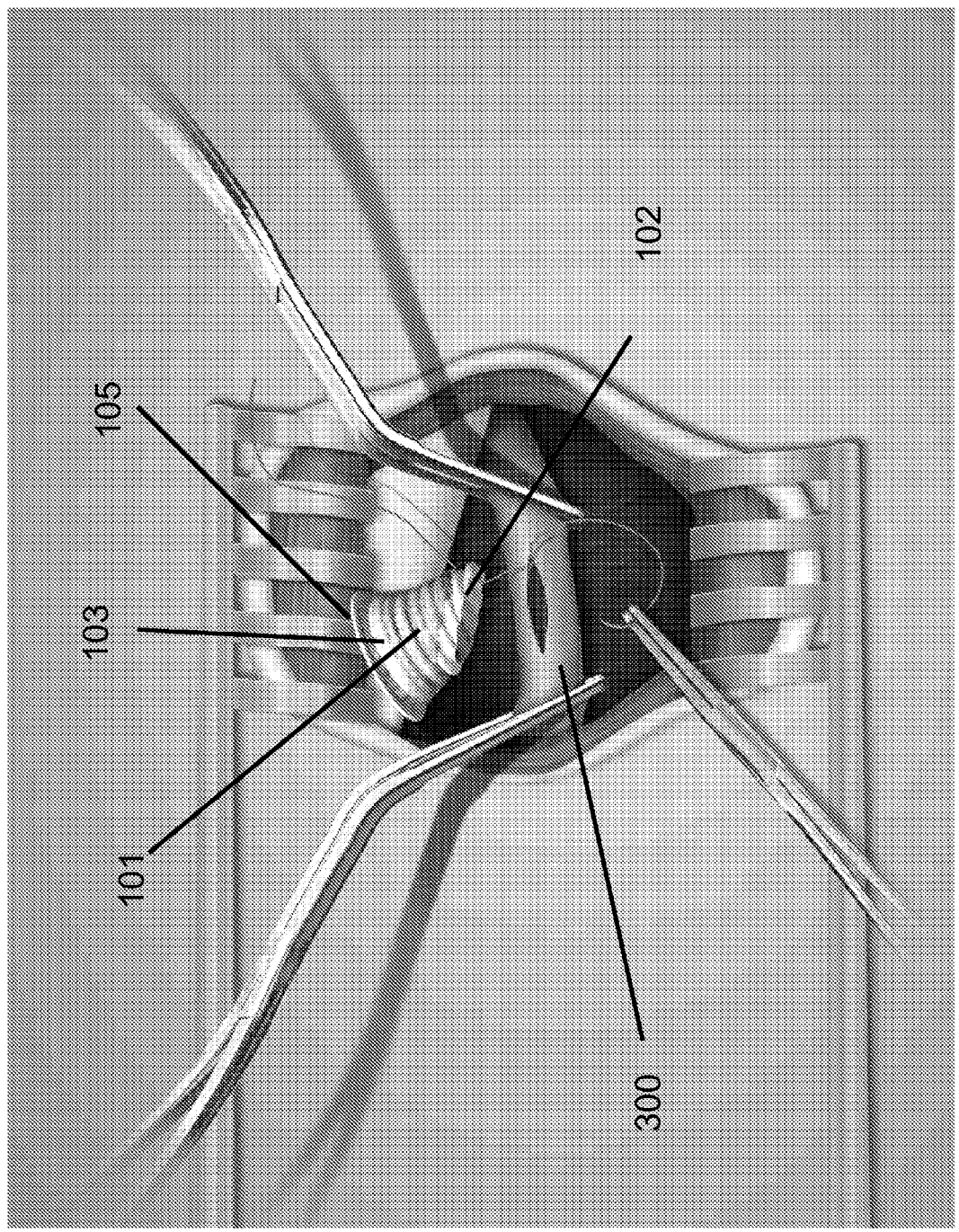

Referring to FIG. 7C, the interposition graft 101 is sewn to the artery 300. In some embodiments, the graft 101 may be flexed or deformed to provide increased visibility of the artery 300.

Figure 7D:
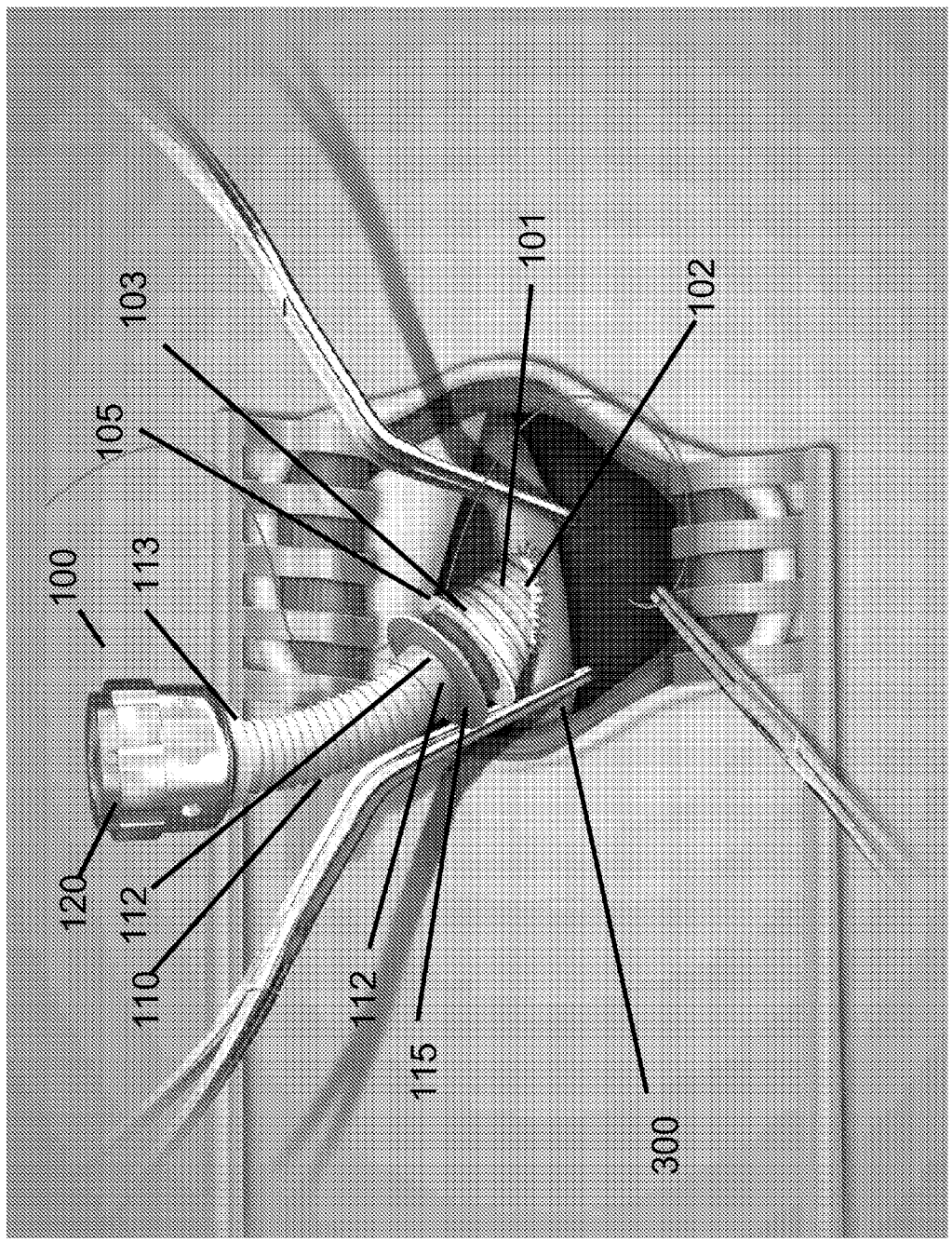

Referring to FIG. 7D, after the interposition graft 101 is attached to the artery 300, a pump graft 110 of appropriate length is selected. The pump graft 110 is attached to the interposition graft using sewing rings 105 and 115. In some embodiments, the grafts 101 and 110 may be pre-marked with indicia to aid in proper alignment. The grafts may also include indicia to guide suturing, to help ensure that the end 112 of the pump graft is properly centered within the inner passage 104 of the interposition graft 101. As noted above, this may promote good washing through the graft and prevent or reduce thrombus formation. In addition these indicia may include additional markings to help keeping the suturing sufficiently dense to provide reliable sealing of the connection. In some embodiments, once the graft 100 has been assembled and attached to the artery, a plug (not shown) may be placed on the open end 113 of the graft (e.g., using the connector 120) to allow for backfilling the graft 100 with blood.

Figure 7E:
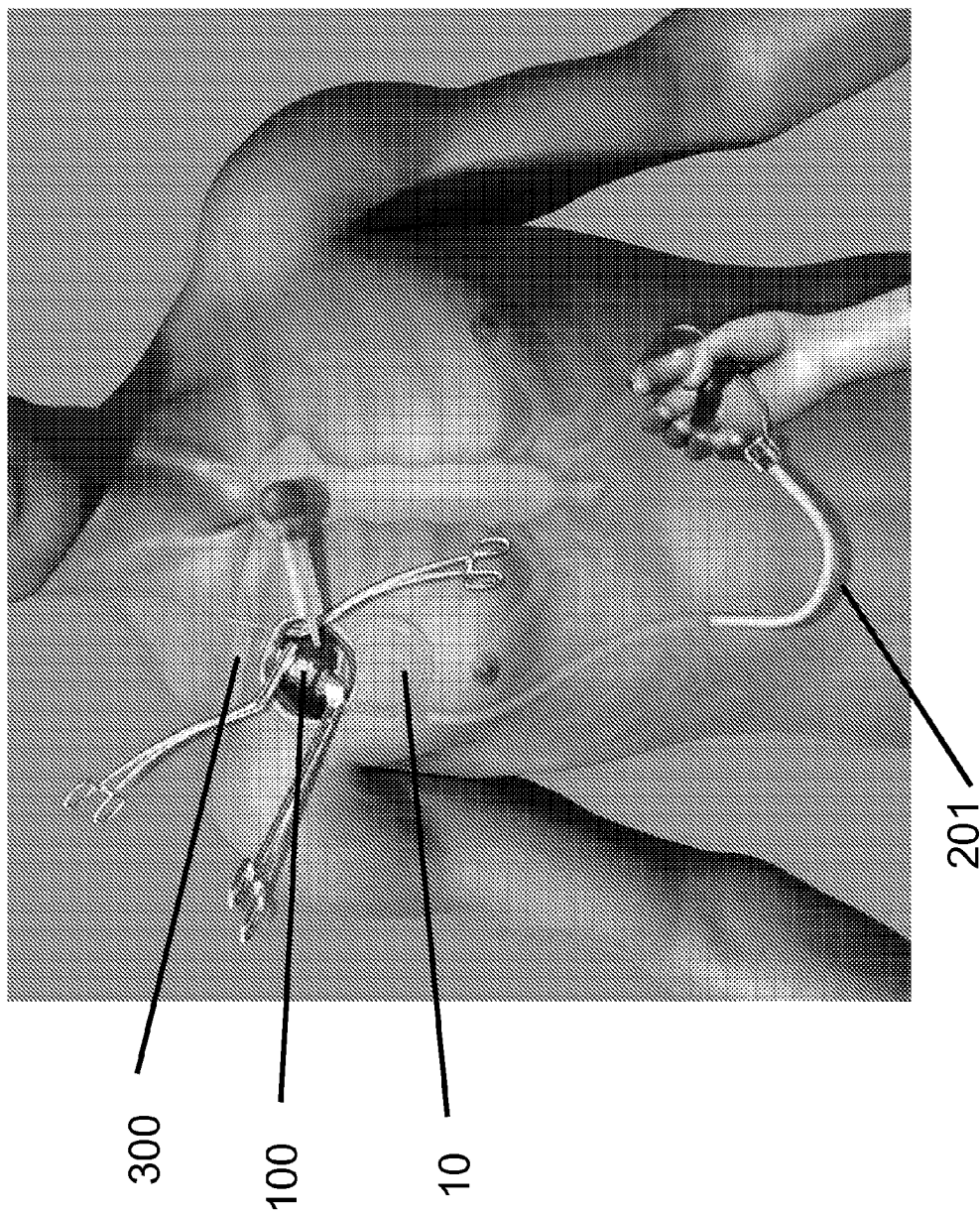

Referring to FIG. 7E, the graft 100 is attached to the pump port 11 of the CPD 10 (e.g., using connector 120 after removal of the plug), and the CPD 10 primed using a hand pump attached to the driveline 201. After checking for air leaks, the driveline may be attached to the drive controller 202, and counterpulsation support commenced.

Figure 7F:
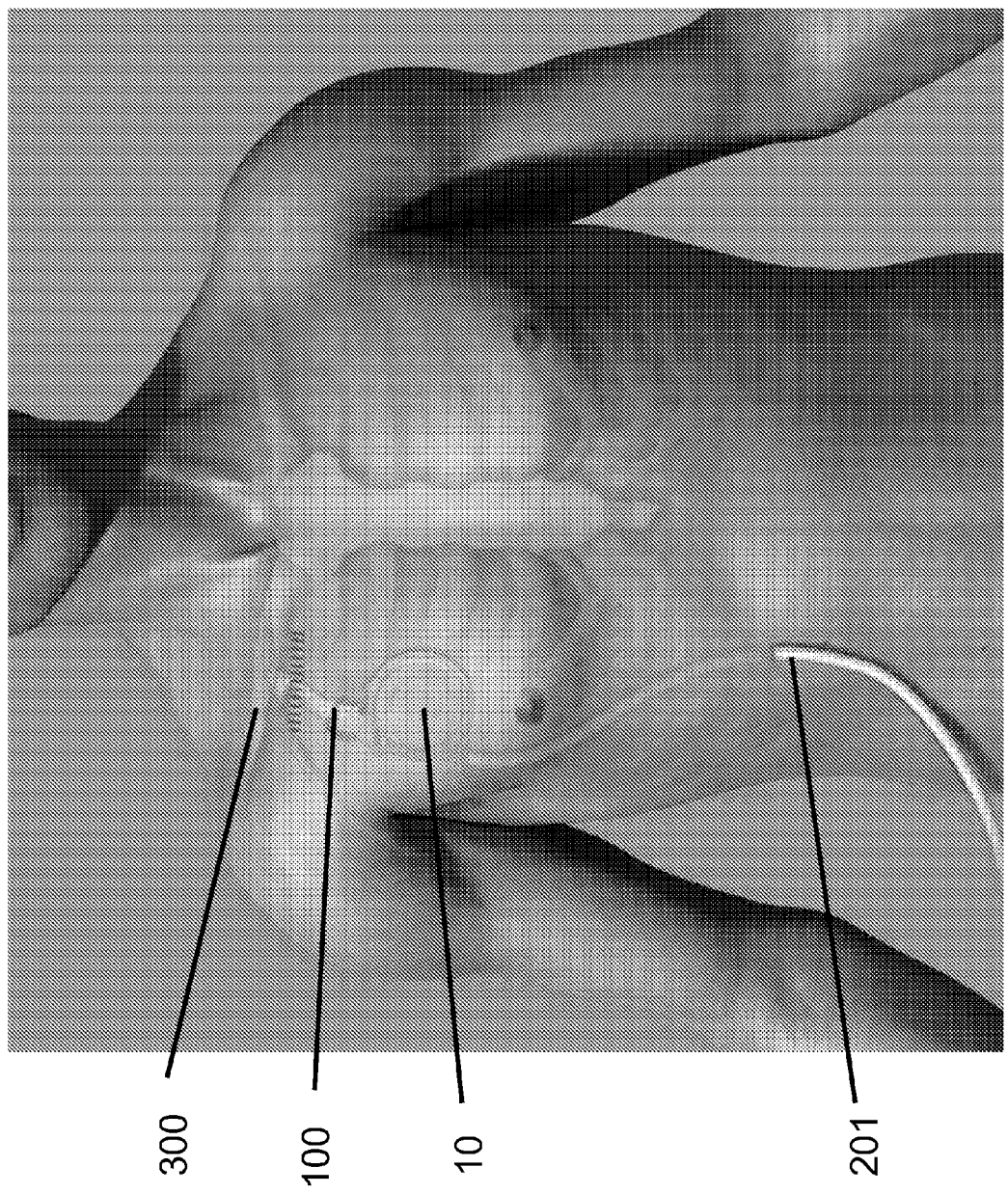

Referring to FIG. 7F, once the proper positioning and operation of the CPD 10 has been confirmed the wound to the pump pocket may be closed.

Although the examples presented above focus on the use of grafts with a CPD device for use in counterpulsation applications, it is to be understood that in various embodiments, grafts of the types described herein may be used with other types of devices and in other applications. In various embodiments, grafts of the types described herein may be advantageously used with various types of blood pumps featuring a single port used for both inflow and outflow of blood.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for attaching a counter pulsation device (CPD) to a blood vessel in a human or animal subject, the apparatus comprising:
    an interposition graft having a first end configured to be attached to the blood vessel, a second end, and an interior passage providing fluid connection between the first end and the second end; and
    a pump graft having first end attached to the second end of the interposition graft, a second end configured to be attached to the CPD, and an interior passage providing fluid connection between the first end and the second end;
    wherein:
    the interior passage of the interposition graft comprises a rough surface configured to promote biological growth on the rough surface;
    the interior passage of the pump graft comprises a smooth surface configured to inhibit biological growth on the smooth surface;
    the interposition graft is shaped to prevent contact between the rough surface and the smooth surface to inhibit biological growth from the rough surface onto the smooth surface; and
    the second end of the interposition graft comprises a first sewing ring, and the first end of the pump graft comprises a second sewing ring, and wherein the first and second sewing rings are configured to be attached to each other.

2. The apparatus of claim 1, wherein the interior passage of the interposition graft has a region of increased diameter located proximal to the second end of the interposition graft configured such that the first end of the pump graft extends into the interior passage of the interposition graft without making physical contact with the rough surface.

3. The apparatus of claim 1, wherein the interposition graft is substantially flexible.

4. The apparatus of claim 1, wherein the rough surface comprises a fabric material.

5. The apparatus of claim 4, wherein the fabric material comprises a fabric comprising polymer fibers.

6. The apparatus of claim 5, wherein the fibers comprise polyester fibers.

7. The apparatus of claim 1, wherein the pump graft comprises an expanded thermoplastic polymer.

8. The apparatus of claim 1, wherein the interposition graft is substantially elastic providing sufficient force maintain an interface between the interposition graft and the vessel open during use.

9. A method for attaching a counter pulsation device (CPD) to a blood vessel in a human or animal subject, the method comprising:
    obtaining an interposition graft having a first end configured to be attached to the blood vessel, a second end, and an interior passage providing fluid connection between the first end and the second end; and
    obtaining a pump graft having first end attached to the second end of the interposition graft, a second end configured to be attached to the CPD, and an interior passage providing fluid connection between the first end and the second end;
    wherein:
    the interior passage of the interposition graft comprises a rough surface configured to promote biological growth on the rough surface;
    the interior passage of the pump graft comprises a smooth surface configured to inhibit biological growth on the smooth surface;
    the interposition graft is shaped to prevent contact between the rough surface and the smooth surface to inhibit biological growth from the rough surface onto the smooth surface; and
    the second end of the interposition graft comprises a first sewing ring, and the first end of the pump graft comprises a second sewing ring;
    the method further comprising:
    attaching the first end of the interposition graft to the blood vessel;
    attaching the second end of the interposition graft to the first end of the pump graft; and
    attaching the second end of the pump graft to the CPD;
    wherein attaching the second end of the interposition graft to the first end of the pump graft comprises sewing the first and second sewing rings to each other.

10. The method of claim 9, wherein the interior passage of the interposition graft has a region of increased diameter located proximal to the second end of the interposition graft, and comprising:
    attaching the second end of the interposition graft to the first end of the pump graft such that the first end of the pump graft extends into the interior passage of the interposition graft without making physical contact with the rough surface.

11. The method of claim 9, wherein the interposition graft is substantially flexible, and further comprising, during the step of attaching the first end of the interposition graft to the blood vessel, flexing the interposition graft.

12. The method of claim 11, wherein flexing the interposition graft comprises flexing the graft to provide increased visibility of the blood vessel.

13. The method of claim 9, wherein the rough surface comprises a fabric material.

14. The method of claim 13, wherein the fabric material comprises a fabric comprising polymer fibers.

15. The method of claim 14, wherein the fibers comprise polyester fibers.

16. The method of claim 9, wherein the pump graft comprises a molded thermoplastic polymer.

17. The method of claim 9, wherein the wherein the interposition graft is substantially elastic providing sufficient force maintain an interface between the interposition graft and the vessel open during use.

18. The method of claim 9 wherein the blood vessel comprises the subclavian artery.

19. The method of claim 9, further comprising implanting the CPD in the subject.

20. The method of claim 19, wherein the CPD is implanted superficially outside of a chest cavity of the subject, and the pump and interposition graft provides fluid communication between the CPD and the blood vessel within the chest cavity.

21. A kit for attaching a counter pulsation device (CPD) to a blood vessel comprising:
    an interposition graft having a first end configured to be attached to the blood vessel, a second end, and an interior passage providing fluid connection between the first end and the second end; and
    a pump graft having first end configured to be attached to the second end of the interposition graft, a second end configured to be attached to the CPD, and an interior passage providing fluid connection between the first end and the second end;

wherein:
the interior passage of the interposition graft comprises a rough surface configured to promote biological growth on the rough surface;
the interior passage of the pump graft comprises a smooth surface configured to inhibit biological growth on the smooth surface;
the interposition graft is shaped to prevent contact between the rough surface and the smooth surface to inhibit biological growth from the rough surface onto the smooth surface; and
the second end of the interposition graft comprises a first sewing ring, and the first end of the pump graft comprises a second sewing ring, and wherein the first and second sewing rings are configured to be attached to each other.

22. The kit of claim 21, wherein the interior passage of the interposition graft has a region of increased diameter located proximal to the second end of the interposition graft configured such that the first end of the pump graft extends into the interior passage of the interposition graft without making physical contact with the rough surface.

23. The kit of claim 21, wherein the interposition graft is substantially flexible.

24. The kit of claim 21, wherein the rough surface comprises a fabric material.

25. The kit of claim 24, wherein the fabric material comprises a fabric comprising polymer fibers.

26. The kit claim 25, wherein the fibers comprise polyester fibers.

27. The kit of claim 21, wherein the pump graft comprises a molded thermoplastic polymer.

28. The kit of claim 21, wherein the interposition graft is substantially elastic providing sufficient force maintain an interface between the interposition graft and the vessel open during use.

29. A system comprising:
a counterpulsation device (CPD);
an apparatus configured for attaching the CPD to a blood vessel in a human or animal subject, the apparatus comprising:
an interposition graft having a first end configured to be attached to the blood vessel, a second end, and an interior passage providing fluid connection between the first end and the second end; and
a pump graft having first end attached to the second end of the interposition graft, a second end configured to be attached to the CPD, and an interior passage providing fluid connection between the first end and the second end;
wherein:
the interior passage of the interposition graft comprises a rough surface configured to promote biological growth on the rough surface;
the interior passage of the pump graft comprises a smooth surface configured to inhibit biological growth on the smooth surface;
the interposition graft is shaped to prevent contact between the rough surface and the smooth surface to inhibit biological growth from the rough surface onto the smooth surface; and
the second end of the interposition graft comprises a first sewing ring, and the first end of the pump graft comprises a second sewing ring, and wherein the first and second sewing rings are configured to be attached to each other.

30. The system of claim 29, further comprising a drive line providing pneumatic communication between the CPD and a CPD driver.

31. The system of claim 30, further comprising the CPD driver.

32. The system of claim 30, wherein the CPD comprises drive chamber in pneumatic communication with the drive line and a blood chamber that is sealed from the drive chamber.

* * * * *